United States Patent [19]

Schimel

[11] 4,375,412
[45] Mar. 1, 1983

[54] METHODS FOR THE TREATMENT OF ORGANIC MATERIAL AND PARTICULARLY SEWAGE SLUDGE

[76] Inventor: Keith A. Schimel, 220 Glen Echo Dr., Norfolk, Va. 23805

[21] Appl. No.: 199,896

[22] Filed: Oct. 23, 1980

Related U.S. Application Data

[63] Continuation-in-part of Ser. No. 3,167, Jan. 15, 1979, abandoned.

[51] Int. Cl.³ ............................................. C02F 3/28
[52] U.S. Cl. .................................. 210/603; 210/609; 210/622; 435/168
[58] Field of Search ............... 210/603, 609, 613, 630, 210/622, 629; 435/168, 267

[56] References Cited

U.S. PATENT DOCUMENTS

| | | | |
|---|---|---|---|
| 1,757,263 | 5/1930 | Sims | 210/188 X |
| 2,029,702 | 2/1936 | Buswell et al. | 210/603 |
| 2,638,444 | 5/1953 | Kappe | 210/603 X |
| 2,786,025 | 3/1957 | Lamb et al. | 210/609 X |
| 4,198,292 | 4/1980 | Snider et al. | 210/603 |

*Primary Examiner*—Thomas G. Wyse
*Attorney, Agent, or Firm*—Martin LuKacher

[57] ABSTRACT

Anaerobic digestion of organic material, particularly biological sludge, such as sewage sludge, is carried out in a closed system having a first digestion tank and a second concentration and partial digestion tank. The concentrated and partially digested sludge is fed to the first tank where it is maintained under vacuum such that an active zone of organic material undergoing digestion is detained therein for a long period of time. The digested sludge is withdrawn against the vacuum and has approximately 80 to 90% of the organic solids therein mineralized; thus simplifying dewatering and ultimate disposal of the sludge. Pathogens including viruses are also removed from the digested sludge. Denitrification takes place in the vacuum digester tank and gas consisting essentially of nitrogen is removed. Return sludge from the vacuum digester and influent sludge is fed into the second or concentrator tank to facilitate reseeding with anaerobic organisms. Both tanks are provided with passageways which are coterminous near the upper ends of the tanks and provided with baffles which direct the flow to be in opposite directions in the passageways, thus providing for stripping of the gas and solid-liquid separation. Gas consisting essentially of methane and carbon dioxide is produced from the second tank. Supernatant from the second tank may be recirculated to the source of the sludge to facilitate degradation of remaining organic contaminants. For the production of ammonia gas, the pressure in the first tank is cycled repeatedly between vacuum and atmospheric or just above atmospheric pressure; the ammonia gas being withdrawn with the digested sludge.

16 Claims, 6 Drawing Figures

METHODS FOR THE TREATMENT OF ORGANIC MATERIAL AND PARTICULARLY SEWAGE SLUDGE

This application is a continuation in part of my application Ser. No. 3,167 filed Jan. 15, 1979, now abandoned.

The present invention relates to a system of and method for sewage treatment, and particularly to anaerobic digestion of sewage sludge or other organic material.

The invention is especially suitable for use in the treatment of waste water for hygienic disposal, as in municipal sewage treatment plants, and provides methods and means for the digestion of sludge which is generated in the course of such treatment.

Of the various approaches to sewage treatment, anaerobic digestion has become an important portion of the treatment facilities. A review of anaerobic sludge digestion may be found in *Manual of Practice No. 16—Anaerobic Sludge Digestion*, published by the Water Pollution Control Federation, Washington, D.C. (1968), and in Document EPA 430/9-76-001 entitled *Operations Manual Anaerobic Sludge Digestion*, published by the U.S. Environmental Protection Agency (1976) and available through the National Technical Information Service, Springfield, Va. and in articles found in the Water Pollution Control Federation Journal, Vol. 26, p. 462–476 (1954), Vol. 27, p. 121–133 (1955), and Vol. 31, (II) p. 164–190 (1959).

Anaerobic digestion as presently practiced has disadvantages. Principal among these disadvantages is that the reduction in volatile organic material is not nearly complete. Only about 40% of the volatile solids are removed and the stabilized (also known as mineralized) sludge obtained from the digester typically has 60% volatile solids as measured by the conventional sludge solids tests (see the above referenced Manual EPA 430/9-76/001, page E9 et seq). Another disadvantage is the hydraulic detention time that the liquid stays in the conventional anaerobic digestion system. Unless the digester is heated, the residence time in the digester is typically 40 to 60 days. Intermittent or batch feeding and withdrawal further complicate the efficiency of sludge processing. Digesters are sensitive to failure and may become "sour", in which case the entire system must be stopped and the digester tank cleaned out and restarted. The environmental effects of such failures may be serious, particularly where other facilities for treatment are unavailable and raw sewage or untreated sludge must be disposed of into the environment. Some thoughts have been reported on increasing the reaction rates in digestion of volatile acid liquids which are retained without flow resident in a tank under vacuum at one end (see Science, Dec. 12, 1975, p. 1088). However, continuous processing for biological conversion of solid, rather than liquid to final stabilized material and gases has not been suggested heretofore.

Nitrogenous compounds are contained in sewage sludge and complex processes have been proposed for denitrification (see *Final Report—Evaluation of Municipal Sewage Treatment Alternatives*, prepared for the Council in Environmental Quality, Executive Office of the President, in Association with the Environmental Protection Agency, Office of Planning and Evaluation (February 1974), which may be obtained from the Superintendent of Documents, U.S. Government Printing Office, Washington, D.C., pages A-62 through A-84). Such processes require complex and expensive facilities, and have not been generally adopted. The present invention has as one of its features and advantages the denitrification of organic material such as sewage sludge, anaerobically, while the material is treated continuously, and at higher rates than with conventional anaerobic digestion processes. Such conventional processes do not produce nitrogen, but are limited to the generation of methane, carbon dioxide and mercaptans. Either nitrogen or ammonia gas or both may be produced in accordance with this invention.

While sludge obtained from conventional anaerobic digestion tanks is relatively free of bacterial pathogens, viruses are normally present in digested stabilized sludge. The method and system of anaerobic digestion provided in accordance with the invention has been discovered to provide digested stabilized sludge which may be free of pathogenic viruses as well as bacteria, to the extent that viral testing has been performed up to the present time.

Accordingly, it is and object of the present invention to provide an improved system of and method for treatment of organic materials such as sewage sludge by biological processes.

It is another object of the present invention to provide an improved method of and system for anaerobic digestion of organic materials and particularly sewage sludge.

It is a further object of the invention to provide an improved system of and method for anaerobic digestion in which the reduction in volatile solids contained in the digested and stabilized material is reduced from approximately 40% to 60%, as in the case of conventional anaerobic sludge digestion, to 80% to 90% or more of the volatile solids in the influent material which is treated.

It is a still further object of the invention to provide an improved system of and method for anaerobic digestion of sewage sludge in which digestion time is reduced, such that the hydraulic loading or residence time of the liquid in the system is reduced substantially from the hydraulic loading or residence time in the case of conventional anaerobic sludge digesters, and continuous feeding of influent and withdrawal of effluent digested sludge is made feasible.

It is a still further object of the present invention to provide an improved system of and method for anaerobic digestion of sewage sludge which is continuous in operation rather than intermittent or batch operated.

It is still a further object of the invention to provide an improved system of and method for anaerobic sludge digestion which enables the continuous removal of digested (viz., stabilized or mineralized) sludge.

It is a still further object of the present invention to provide an improved method of and system for anaerobic digestion of sludge in which digestor failure possibilities are reduced and the consequent need for shutdown, clean-out, and restarting of the digester is minimized.

It is a still further object of the invention to provide an improved method of and system for anaerobic digestion of sewage sludge whereby the sludge is disinfected of pathogenic bacteria and may also be disinfected of pathogenic viruses.

It is a still further object of the present invention to provide an improved system of and method for anaerobic digestion of organic materials such as sewage sludge which denitrifies the material and provides a source of nitrogen and/or ammonia gas.

Briefly described, the system of and method for the treatment of slurries of organic material, such as sewage sludge, in accordance with the invention makes use of a tank in which anaerobic conditions are established. By means of pumps associated with the tank, regions below atmospheric pressure are provided at opposite ends of the tank. The material to be treated may be any biological sludge, such as activated sludge, and preferably is partially digested and concentrated sludge from another tank in which concentration and anaerobic digestion takes place and which is connected to the first mentioned digester tank in a closed system. The sludge is fed continuously and preferably through the closed system into the tank which is at vacuum. The rate or velocity of feeding is such that an active zone containing a submerged suspension of solids of the organic material is formed in the tank. As the material stabilizes, it falls to the bottom of the tank and is drawn off as by a pump. Gas, which may be in the form of nitrogen, is stripped from submerged solids and from the liquid as it circulates through the tank. Baffles disposed at the end of passageways formed in the tank for the flow of the liquid are preferably used to facilitate the stripping of the gas. The gas removed may consist essentially of nitrogen. By cycling the pressure in the digester between vacuum and atmosphere or above atmospheric pressure, ammonia gas may be produced and released. The digested sludge has a high content of stabilized material with volatile solids reduced to from 40% to at least 80% of the volatile solids contained typically in influent sewage sludge from a source such as an aerobic mixing tank of a secondary treatment system. The digested sludge has been found to be essentially free of pathogens including viruses.

The foregoing and other objects, features and advantages of the invention as well as the best mode now known for practicing the invention and a preferred embodiment thereof will be more apparent from a reading of the following description in connection with the accompanying drawings in which.

Figure 1:
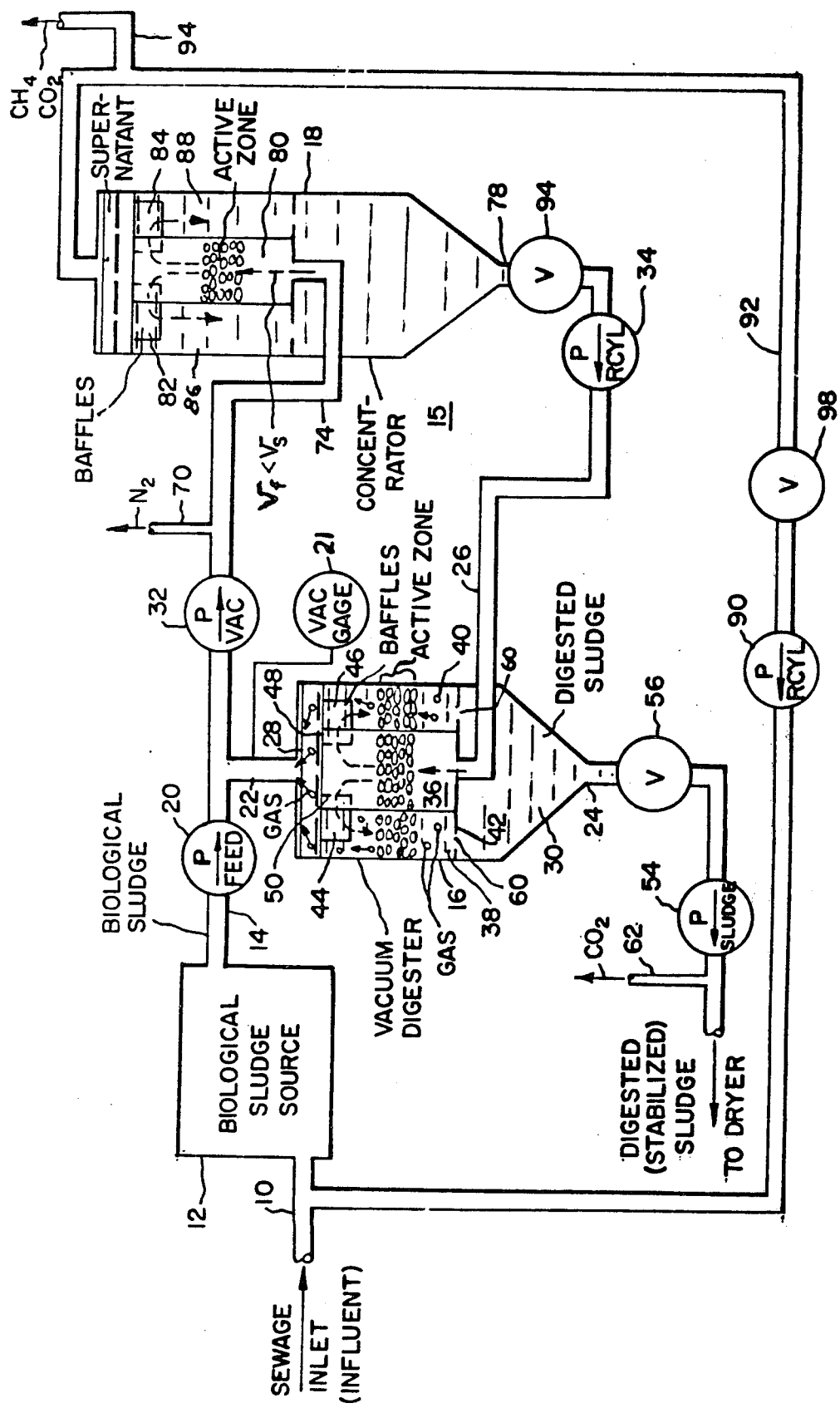
FIG. 1 is a diagram schematically showing an anaerobic sludge digestion system in accordance with the invention.
Figure 2:
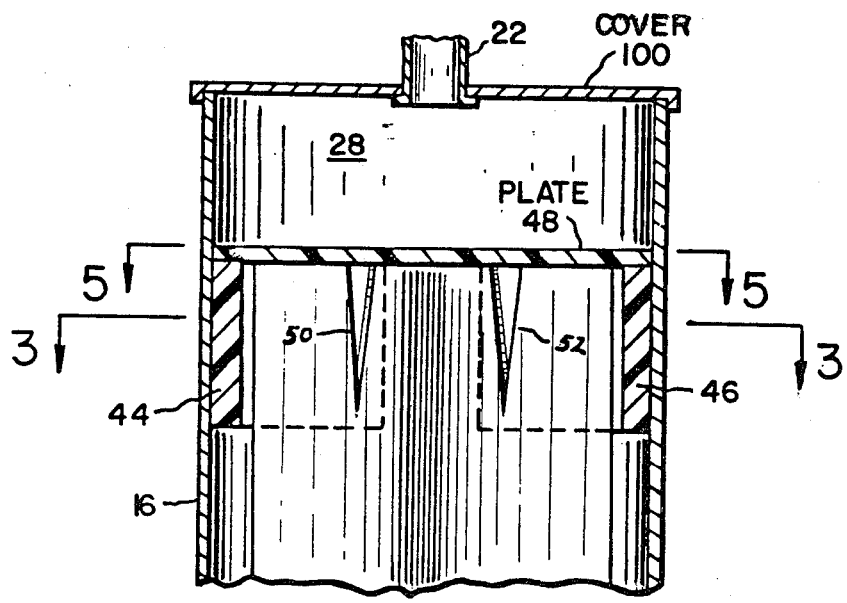
FIG. 2 is a fragmentary view in elevation of the upper portion of one of the tanks in the system of FIG. 1.
Figure 3:
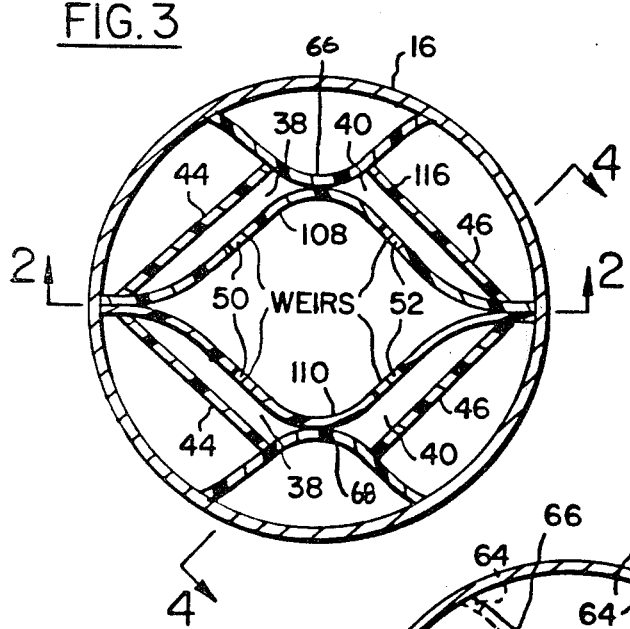
FIG. 3 is a sectional plan view of one of the tanks, the view being taken along the line 3—3 in FIG. 2.
Figure 4:
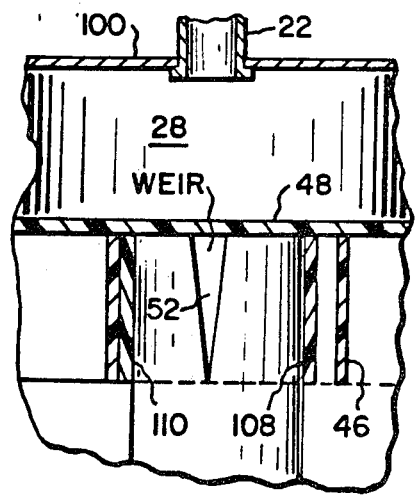
FIG. 4 is a fragmentary sectional view of one of the tanks, the view taken along the line 4—4 in FIG. 3.

Referring more particularly to FIG. 1, there is shown a biological sludge source 12. The source 12 may be waste sludge from a biological treatment unit, such as a primary clarifier sludge, activated sludge, trickling filter waste sludge and the like. For example, sewage which has preferably undergone primary treatment to remove grit is fed into an inlet 10 and into a secondary treatment system which may include the conventional clarifier, such as filters or sedimentation chambers and aerator tanks which provide the source of biological sludge. This sludge may be activated sludge. This source 12 is shown diagrammatically in FIG. 1. The output from the source is obtained from an outlet 14 near the top of a tank and is fed continuously into a closed loop system 15 containing two tanks 16 and 18 in which anaerobic digestion of the sludge takes place. A pump 20 which may suitably be of the constant displacement type feeds the sludge into the closed loop system 15. The tank 16, which is referred to herein as the vacuum digester, outputs digested (viz. stabilized and mineralized) sludge. This digested sludge may be filtered or further purified. This sludge contains liquid high in ammonia and may alternatively be used as a fertilizer and applied to the land. The tank 18 is referred to as the concentrator.

The tanks 16 and 18 and the lines interconnecting them are preferably constructed of material which is non-biodegradable. In small scale systems, acrylic plastic material may be used.

The vacuum digester tank 16 has outlets 22 and 24 at opposite ends thereof. The tank 16 is preferably maintained with its longitudinal axis vertical. The lower end of the tank may be conical in shape. The tank 16 is also provided with an inlet 26 for the concentrated and partially digested sludge from the concentrator tank 18. This inlet enters the tank 16 between the region 28 at the top of the tank and a region 30 at the bottom of the tank. The pressure in the top region 28 is below atmospheric pressure and is a vacuum. The vacuum is maintained by a pump 32 which is operated at a faster rate than the feed pump 20. The gauge 21 measures the vacuum in the region 28. A suitable vacuum pressure depends upon the scale of the system. In a small scale system a vacuum pressure of about $-50$ centimeters of mercury (gage pressure) has been found suitable. The optimum vacuum range is between $-30$ to $-50$ cm Hg gage vacuum. The amount of vacuum needed to maintain the solids in suspension is dependent on the character of the solid (i.e., the solid biodegradiability).

The concentrated sludge from the concentrator tank 18 is fed into the inlet 26 of the vacuum digester tank 16 by a pump 34, which may also suitably be a constant displacement pump. In the tank 16, partitions form a plurality of passageways between the bottom and top regions 30 and 28 of the tank 16. A central passageway 36 and two passageways 38 and 40 which are adjacent thereto, are shown in FIG. 1. A plate 42 with holes 60 therethrough, is disposed at the bottom of the passageways and an arrangement of baffles 44 and 46 attached to an upper plate 48 are disposed at the top of the passageways 36, 38 and 40.

The concentrated sludge from the inlet enters through the bottom plate 42 into the central passageway 36. The liquid in the sludge flows in the direction shown by the arrows on the dash lines through openings 50 and 52 (see FIGS. 2 to 5). A submerged suspension of solid particles or retained in an active zone. These openings 50 and 52 are in the form of weirs at the partitions between the center passageway 36 and the passageways 38 and 40 adjacent thereto. The flow against the vacuum is obtained by gravity and by applied vacuum from another pump 54 which withdraws the digested sludge, which is the effluent from the closed loop 15, from the lower region 30 of the tank 16. This sludge pump 54 may also be a constant displacement pump. The flow and pressure is adjusted by means of a valve 56.

Figure 6:
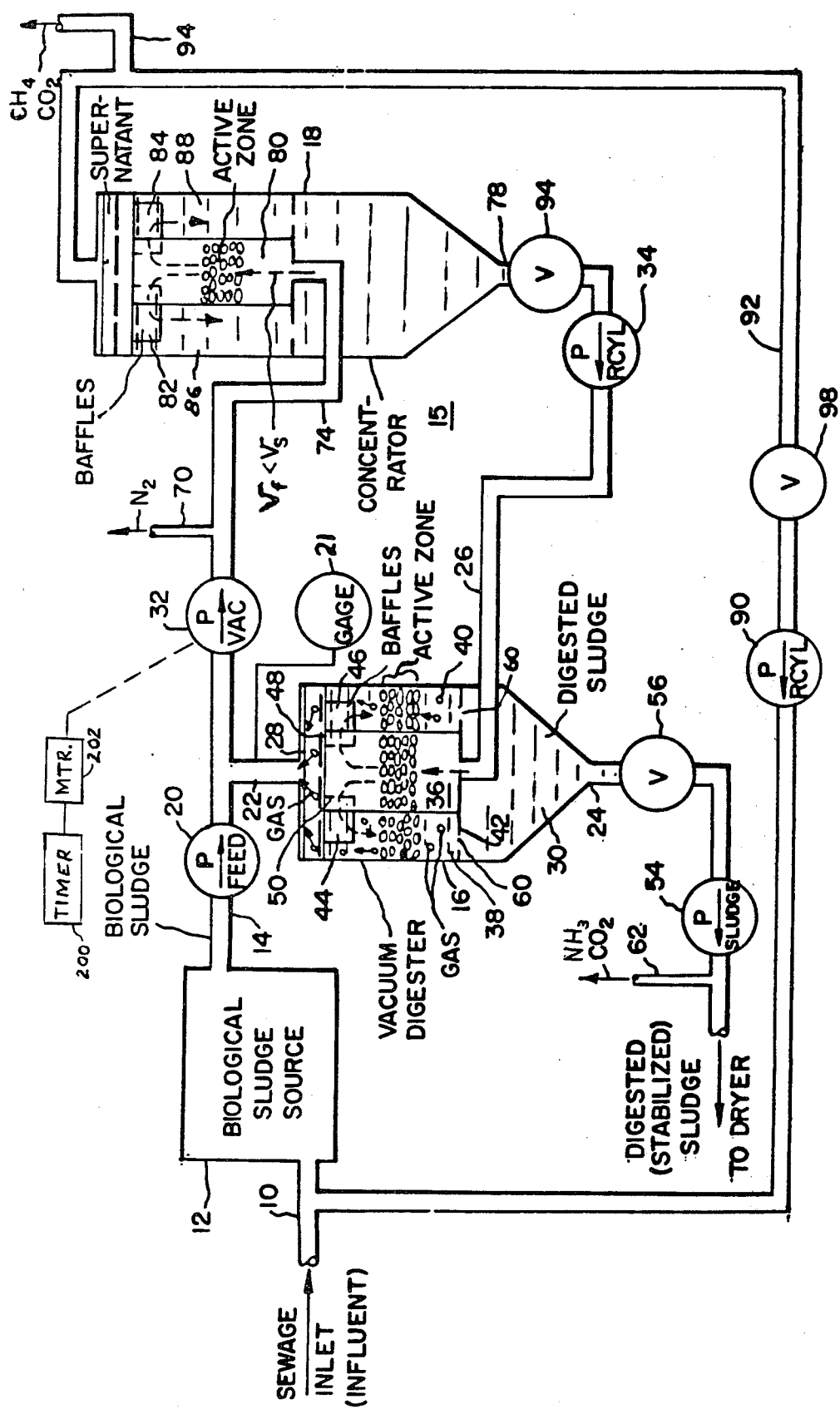
FIG. 6 is a diagram of an anaerobic digestion system in accordance with another embodiment of the invention.

Inasmuch as the sludge source 12 is open to the air and this source 12 is connected to the concentrator tank 18, the concentrator tank and the portion of the system between the vacuum pump 32 and the concentrator tank 18 is at atmospheric pressure. The vacuum digester tank 16 is below atmospheric pressure and maintained at vacuum by the vacuum pump 32 or may be cycled between alternate periods at vacuum and at or above atmospheric pressure, as shown in FIG. 6. After the system is in operation, all air is withdrawn and anaerobic conditions are established and continue to exist so long as the system is in operation.

The vacuum established in the upper region 28 maintains the volatile organic solids in suspension in an active zone in the passageways 36, 38 and 40, thus concentrating the solid mass. As the solid volume is reduced (stabilized) by microbial action, the incoming solids from passageway 36 fill the void volume thus continuously concentrating the solids in the reactor. While the vacuum and the low specific gravity of the volatile organic solids tends to make them rise, a small vacuum exerted by the sludge pump 54, tends to bring the liquid and mineralized suspended particles downward. The pressures are adjusted such that the volatile organic solids are maintained in the active zone for an extremely long period of time until the action of the anaerobic bacteria stabilizes and mineralizes them. The solids become heavier as mineralization progresses. The increased specific gravity is also due, it is believed, because of gas molecules which have a higher probability of attaching to the volatile organic solids than to the stabilized and mineralized solids. The stabilized and mineralized solids then move downward through the outside passageways 38 and 40, through openings 60 in bottom plate 42 and into the conical lower region whence they are withdrawn with the liquid through the outlet 24. A gas outlet 62 for the withdrawal of gas which may be released from the digested sludge is provided at the outlet side of the sludge pump 54. This gas has been found to consist essentially of carbon dioxide ($CO_2$), with ammonia ($NH_3$) being produced when the pressure is cycled (See FIG. 6).

As the volatile organic materials in suspension in the active zone are digested, gas is released. Further, as the liquid flows through the weirs 50 and 52 at the upper end of the passageways 36, 38 and 40 and is deflected by the baffles 44 and 46, gas is stripped from the liquid. This gas is drawn by the vacuum in the upper region 28 through openings shown as notches 64 in two of the partitions 66 and 68 which form the passageways 36, 38 and 40 (see FIG. 5). The gas has been found to consist essentially of nitrogen ($N_2$) with some methane ($CH_4$) released from time to time in small amounts. This gas may be withdrawn through a gas outlet 70 on the pressure side of the vacuum pump 32.

The exact biological or other process which takes place in the vacuum digester tank 16 so as to release nitrogen gas from the upper outlet 22 (or ammonia gas from the outlet 62 when the pressure is cycled) and digested sludge of low volatile organic solid content from the lower outlet 24 is not fully understood at the present time. The conditions which results in the operation, namely the vacuum anaerobic condition in the digester tank 16 and the influx and withdrawal of the sludge into the tank continuously have been found, quite unexpectedly, to provide high solids destruction during short hydraulic residence time, typically 30 hours hydraulic loading or residence time in the system, as compared to 40 to 60 days in conventional anaerobic digesters. The system is operated to provide these results at room temperature, approximately 68° F. (20° C.±1° C.). Higher temperatures may be used. A high concentration of anaerobic organisms, from the upper region 28 of the vacuum digester tank 16, are recycled and mixed with the incoming raw sludge metered through feed pump 20, and applied to the concentrator tank 18 through inlet 10 from the upper region 28 of the vacuum digester tank is applied to the concentrator tank 18 through an inlet 74. The tank 18 also has top and bottom outlets 76 and 78, and is oriented with its longitudinal axis vertical. The bottom of the tank may be conical in shape. The tank also has an arrangement of partitions, plates and baffles, similar to the arrangement used in the vacuum digester tank 16. The influent activated sludge mixture from the vacuum digester tank 16 is fed through a central passageway 80, forming an active zone, and is diverted by baffles 82 and 84 into adjacent passageways 86 and 88. The liquid flow is in the direction shown by the arrows on the dash lines. The baffles 82 and 84 assist in stripping the gas which together with the supernatant flows through the outlet 76. The supernatant may be recycled back into the activated sludge unit by means of a recycling pump 90 through the feed lines 92. A gas outlet 94 for the methane and carbon dioxide resulting from the partial digestion of the sludge in the tank 18 is also provided. The velocity of flow of liquid through the passageways 80, 86 and 88 is controlled by means of valves such as the valve 94 between the outlet 78 and the recycling pump 34. The velocity of this flow, $v_f$, is suitably less than the settling rate, $v_s$, for solid particles through water. This settling rate is approximately 2.7 centimeters per second. Slower flows for the liquid may be used but preferably the flow should not exceed the settling rate for solid particles. This enables the solid particles to concentrate both by bioflocculation and sedimentation.

Concentrated and partially digested sludge from the tank 18 is recycled by the pump 34 to the inlet 26 of the digestion tank. A concentration of 6 to 10 times in terms of the solids content of the sludge is obtained in the concentrating tank 18. For example, the influent sludge at the outlet 14 of the source may have a concentration of 2500 milligrams per liter of solids material, while the sludge which is obtained at the outlet 78 of the tank 18 has a concentration of 12,000-30,000 milligrams per liter approximately. This tank is maintained at approximately atmospheric pressure.

The system operates continuously with the rates of flow adjusted such that the digested and stabilized sludge content in terms of volatile solids is 80% to 90% less than the volatile solids in the activated sludge influent obtained at the outlet 14 of the source 12. In the event that the volatile solids concentration varies, the rates of flow are adjusted by means of the valves 56 and 94. In the event that the recycling of the supernatant from the top of the concentrator tank 18 is used (such recycling is optional and is desirable when additional dissolved organic contaminant removal is needed), its flow is adjusted by the valve 98. It will be observed that the closed loop affords a feedback signal with error control in terms of the volatile solids content of the digested stabilized sludge. While volatile solids tests may be performed intermittently and adjustments of flow rate made intermittently, continuous testing and automatic adjustment may be implemented through feedback control techniques of the type used in electrical servo systems.

The construction of the passageways and baffling arrangements in the tanks is shown in FIGS. 2 through 5. Considering the tank 16 for example, since the arrangement of passageways and baffles is similar in both tanks 16 and 18, it will be observed that the tank is closed by a cover 100 at the upper end thereof where the outlet is located.

Figure 5:
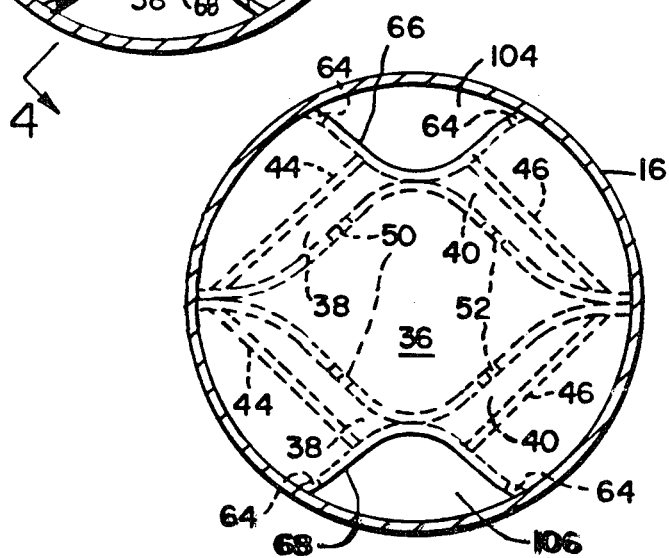
FIG. 5 is another sectional plan view taken along the line 5—5 in FIG. 2.

The plate 48 is disposed below the top of the tank to provide the region 28 for the escape of the gas and active sludge through the outlet 22. This region is maintained at vacuum by the pump 32. The plate has convolute cut-away sections which conform to the shape of the partitions 66 and 68 which form walls of the side passageways 38 and 40. These cut-away sections are indicated at 104 and 106 in FIG. 5. The baffles 44 and 46 extend between the partitions 66 and 68 and partitions 108 and 110 which are convolute in shape and form the walls of the central passageway 36 and the passageways 38 and 40 which are adjacent thereto. There partitions are defined by sheets. The sheets form a honeycomb in cross-section (see FIG. 3) and define the passageways therethrough. In other words, the honeycomb is in a plane perpendicular to the length of the passageways. The weirs 50 and 52 are triangular notches in the partitions 108 and 110. The flow of liquid is through these weirs into the passages 38 and 40. Deflection ocurs at the baffle plates 44 and 46. Gas which is stripped from the liquid at the baffle plates exists through small notches 64 (FIG. 5). The cover plate 48 and also the bottom plate 42 may be made of acrylic material. The partitions may be made of another non-reactive plastic such as from sheets of polyvinyl chloride. The partitions may be cemented together with epoxy cement or heat welded to form a unitary assemblage.

Referring to FIG. 6, there is shown a system similar to the system described in connection with FIGS. 1-5. The pump 32 is run in repeated cycles to produce faster flow for about seven hours and slower flow for about one hour. The applied vacuum period and amplitude of applied vacuum pressure will vary depending upon the characteristics of the solid organic matrix and will be adjusted accordingly. A timer 200 which changes the speed of a pump drive motor 202 after about a one hour period and then after about a seven hour period may be used. The timer may control the motor drive current or voltage. As a result of the change in flow more or less sludge (liquid) is fed into the vacuum digester tank 16, thereby increasing and decreasing the pressure therein between a pressure below atmospheric (a vacuum which may be about 380 TORR) and a pressure at or about atmospheric pressure (suitably about 816 TORR). Then ammonia gas (NH$_3$) is withdrawn with the digested sludge at the outlet 62. The N$_2$ gas at outlet 70 is then reduced in quantity.

From the foregoing description it will be apparent that there has been provided an improved method of and system for the anaerobic digestion of organic materials and particularly sewage sludge. While exemplary forms of the system and the best mode now known for operating the system and practicing the method has been described, it will be appreciated that variations and modifications within the scope of the invention and particularly which are designed to obtain the advantages and new results of low hydraulic residence time and loading, the production of nitrogen and/or ammonia gas and the production of digested stabilized sludge of low volatile solids content will undoubtedly suggest themselves to those skilled in the art. Accordingly, the foregoing description should be taken as illustrative and not in any limiting sense.

I claim:

1. The method for anaerobic digestion of slurries of organic material influents which comprises the steps of anaerobically concentrating and partially digesting said influent material in a concentrator tank at atmospheric pressure while forming a submerged suspension of solids of said material therein, stripping gas resulting from digestion in said submerged suspension in said concentrator tank, introducing the concentrated and partially digested material from said concentrator tank into a vacuum digester tank in a direction to flow through a submerged suspension of active material therein, controlling the flow through said concentrator tank and through said digester tank and between said tanks to maintain the submerged suspension therein, anaerobically digesting said concentrated and partially digested sludge into a stable portion which is substantially mineralized to 80% or more while said submerged suspension of active material is maintained in said vacuum digester tank, and stripping gas resulting from digestion from said submerged suspension of active material in said vacuum digester tank.

2. The method as set forth in claim 1 including the step of continuously recycling the portion of said material in said vacuum digester tank above said submerged suspension together with the influent material to said concentrator tank.

3. The method as set forth in claim 2 further comprising the step of establishing pressures below atmospheric pressure at opposite ends of said vacuum digester tank such that said solids are maintained in said submerged suspension in said vacuum digestor tank while liquid and said mineralized portion exits from one of the opposite ends of said tank and said stripped gas and recycled portion exits from the other of said opposite ends thereof.

4. The method as set forth in claim 3 wherein said pressure establishing step is carried out by maintaining in said vacuum digester tank a pressure between 30 and 50 cm. Hg gage vacuum.

5. The method as set forth in claim 3 wherein said step of anaerobically concentrating and partially digesting said material in said concentrator tank is carried out by introducing said material therein at such a velocity that said submerged suspension is formed and maintained in said concentrator tank and particles of said solids slowly concentrate by both bioflocculation and sedimentation.

6. The method as set forth in claim 5 including the steps of continuously introducing said influent material into said concentrator tank, and continuously withdrawing said liquid and mineralized material from said vacuum digestor tank.

7. The method as set forth in claim 6 further comprising the steps of channeling the flow of liquid in opposite directions in each of said tanks, and diverting, near the ends of said tanks where said gas is stripped, the flow between said opposite directions.

8. The method as set forth in claim 7 wherein said diverting step includes the step of baffling the flow where said liquid is submerged and where said gas is stripped so as to assist in stripping said gas in the submerged environment.

9. The method as set forth in claim 3 wherein said pressure establishing step in said vacuum digestor tank is carried out with said pressure at said other of said opposite ends where said gas is stripped further below atmospheric pressure than at said one of said opposite ends where said mineralized material is withdrawn.

10. The invention as set forth in claim 3 wherein said vacuum is from −30 to −50 cm. Hg gage pressure.

11. The method as set forth in claim 10 wherein said influent material to be treated and which is introduced into said concentrator tank is sludge which is obtained from a source thereof, and further comprising the step of recycling supernatant obtained from said concentrator tank from the sludge upon concentration and partial digestion therein to said source.

12. The method for anaerobic digestion of slurries of organic material influents, such as sewage sludge which comprises the steps of feeding said influent along a line connected to one end of a vacuum digester tank and into a region between the ends of a concentrator tank and forming a submerged suspension of solids of said material therein, feeding a concentrated and partially digested portion of said material from said concentrator tank into a region between the ends of said digester tank and forming a submerged suspension of said material therein repeatedly cycling the pressure within said digester tank between pressures below and at or above atmospheric pressure, and withdrawing a stable portion of said sludge which is substantially mineralized to 80% or more together with ammonia gas from the end of said digestor tank opposite to said one end thereof.

13. The method as set forth in claim 12 wherein said cycling step is carried out by changing said digester tank pressure from below atmospheric pressure to, at or above atmospheric pressure after about seven hours and then changing said digester tank pressure from a pressure at or above atmospheric pressure to below atmospheric pressure after about one hour.

14. The method as set forth in claim 13 wherein said cycling step is carried out with said above atmospheric pressure at about 816 Torr and said below atmospheric pressure at about 380 Torr.

15. The method of production of ammonia gas from the digestion of an influent biological sludge which comprises the steps of first anaerobically partially digesting and concentrating said sludge, and then anaerobically digesting said partially digested and concentrated sludge under a pressure which cycles between vacuum and atmospheric or above atmospheric pressure.

16. The method as set forth in claim 15 wherein said cycles repeat and have alternating periods of about 380 and 816 Torr.

* * * * *